United States Patent

Tahara et al.

Patent Number: 4,598,093
Date of Patent: Jul. 1, 1986

[54] 4-AMINO-TETRAHYDRO-2-NAPHTHOIC ACID DERIVATIVES

[75] Inventors: Tetsuya Tahara, Oita; Masafumi Arita, Tokyo; Tsuyoshi Kuroda, Oita, all of Japan

[73] Assignee: Yoshitomi Pharmaceutical Industries, Ltd., Osaka, Japan

[21] Appl. No.: 609,083

[22] PCT Filed: Aug. 30, 1983

[86] PCT No.: PCT/JP83/00285

§ 371 Date: May 7, 1984

§ 102(e) Date: May 7, 1984

[87] PCT Pub. No.: WO84/00957

PCT Pub. Date: Mar. 15, 1984

[30] Foreign Application Priority Data

Sep. 7, 1982 [JP] Japan .................. 57-155584
Sep. 7, 1982 [JP] Japan .................. 57-155585

[51] Int. Cl.⁴ ............... A61K 31/215; A61K 31/195; A61K 31/165; C07C 103/22
[52] U.S. Cl. .................. 514/538; 514/567; 514/619; 560/47; 562/456; 564/163
[58] Field of Search ........... 560/34, 47; 562/439, 562/456; 424/309, 308, 319, 315; 564/163; 514/538, 567, 619

[56] References Cited

U.S. PATENT DOCUMENTS 3,953,506  4/1976  Spicer et al. .................. 564/56
3,978,124  8/1976  Fried et al. .................. 564/172

FOREIGN PATENT DOCUMENTS 43-22097  9/1968  Japan.

OTHER PUBLICATIONS

Lipschitz et al, *J. Pharmacol. Exp. Therap.*, vol. 79, pp. 97–110 (1943).
Topliss, *J. Med. Chem.*, vol. 20, No. 4, pp. 463–469, (1977).
Topliss, *J. Med. Chem.*, vol. 15, No. 10, pp. 1006–1011, (1972).
Willard et al, *Arch. Int. Pharmacodyn.*, vol. 173, pp. 11–15, (1968).
Loscher, *Arch. Int. Pharmacodyn.*, vol. 257, pp. 32–58, (1982).
Kometani et al, *J. Med. Chem.*, vol. 21, pp. 1105–1110, (1978).
Shiotani et al, *Chemical and Pharmaceutical Bulletin*, vol. 14, No. 4, pp. 324–329, 1966.

*Primary Examiner*—Natalie Trousof
*Assistant Examiner*—Bruce D. Gray
*Attorney, Agent, or Firm*—Sughrue, Mion, Zinn, Macpeak & Seas

[57] ABSTRACT

4-Amino-1,2,3,4-tetrahydro-2-naphthoic acid derivative of the formula:

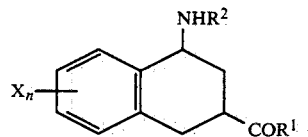

wherein X is halogen atom, n is 1 or 2, $R^1$ is hydroxy group, lower alkoxy group or amino group, and $R^2$ is hydrogen atom, lower alkanoyl group or carbamoyl group, or their salts, which are useful as hypotensive diuretic.

9 Claims, No Drawings

4-AMINO-TETRAHYDRO-2-NAPHTHOIC ACID DERIVATIVES

TECHNICAL FIELD AND DISCLOSURE OF INVENTION

This invention relates to novel and therapeutically useful 4-amino-1,2,3,4-tetrahydro-2-naphthoic acid derivatives of the formula:

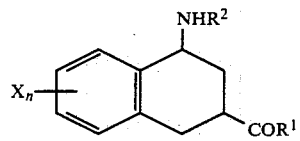

and salts thereof, wherein X is halogen atom, i.e. fluorine, chlorine, bromine or iodine; n is 1 or 2; $R^1$ is hydroxy group, lower alkoxy group, e.g. methoxy, ethoxy, propoxy, isopropoxy, butoxy, isobutoxy, etc. or amino group; and $R^2$ is hydrogen atom, lowr alkanoyl group, e.g. acetyl, propionyl, isopropionyl, butyryl, isobutyryl, etc. or carbamoyl group.

Japanese Patent Publication No. 43-22097 (1968), Chem. Pharm. Bull., 14, 324 (1966) and J. Med. Chem., 21, 1105 (1978) make mention of compounds useful as an intermediate for the synthesis of a certain kind of analgesics, which compounds are represented by the formula:

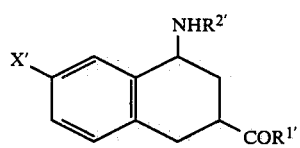

wherein X' is hydrogen atom or methoxy group, $R^{1'}$ is hydroxy group or lower alkoxy group, and $R^{2'}$ is hydrogen or lower alkanoyl group.

The present inventors have synthesized a variety of the derivatives having gamma-aminobutyric acid (hereinafter abbreviated as GABA) moiety in their structure and investigated into their usefullness. As a result, this invention has been accomplished on the basis of the new finding that the compounds of the invention unexpectedly have potent diuretic and blood pressure lowering actions, although they show little protecting effects on the functions in which only the central nervous system participates such as convulsions or fatal convulsions induced by a GABA antagonist such as bicuculline or picrotoxin.

To the contrary, with the aforementioned known comounds these actions are extremely weak or are not substantially apparent.

The compounds of formula (I) wherein $R^2$ is hydrogen can be produced for example by the following Methods 1 to 3:

Method 1

Method of reducing an oxime compound of the formula:

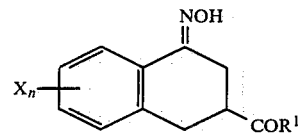

wherein X, n and $R^1$ are the same as defined above. Preferably, catalytic reduction is carried out in the presence of a metallic catalyst such as Raney nickel, platinum oxide or palladium carbon in an inert solvent, preferably a lower alkanol such as methanol, ethanol or the like or a lower alkanoic acid such as acetic acid, if desired in the presence of ammonia for prevention of possible polymerization, at a temperature of room temperature to 150° C., preferably 50° to 100° C. under normal pressure or 50 to 150 atm of hydrogen. Here, hydrogen or hydrazine may be used as a hydrogen source. Otherwise, the reduction may be carried out by the use of metallic sodium in liquid ammonia containing methanol or by the use of both hydrochloric acid or acetic acid and zinc or tin.

Method 2

Method of subjecting a compound of the formula:

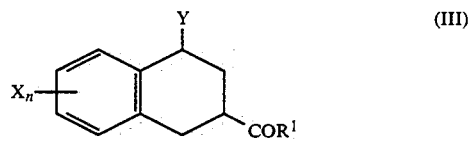

to ammonolysis in water or lower alkanol, wherein X, n and $R^1$ are the same as defined above, and Y is halogen atom, methylsulfonyloxy group, p-tolylsulfonyloxy group or a like reactive residue.

Method 3

Method of subjecting a compound of the formula:

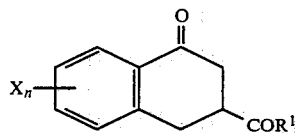

to Leukart reaction, wherein X, n and $R^1$ are the same as defined above. That is, a compound of formula (IV) and urea, ammonium formate or the like undergo fusion reaction in the presence of formic acid at 150°-200° C. and the resulting product is hydrolyzed to give the intended compounds.

The compounds of formula (I) wherein $R^2$ is hydrogen are allowed to react with a reactive derivative of lower alkanoic acid such as acid halide, acid anhydride or the like to give the compounds of formula (I) wherein $R^2$ is lower alkanoyl group. They are allowed to react with potassium cyanate or sodium cyanate in an aqueous lower alkanol to give the compounds of formula (I) wherein $R^2$ is carbamoyl.

The compounds of formula (I) wherein $R^1$ is hydroxy group are allowed to esterify with a lower alkanol in the presence of mineral acid such as hydrochloric acid or sulfuric acid to give the compounds of formula (I) wherein $R^1$ is lower alkoxy. The ester compounds thus obtained or their free carboxylic acids are allowed to react with ammonia to give the compounds of formula (I) wherein $R^1$ is amino.

The N-lower alkanoyl compounds and the ester compounds or the amido compounds each of formula (I) are subjected to hydrolysis to give, reversely, the amino compounds and the free carboxylic acids of formula (I), respectively.

The compounds of formula (I) of this invention produced in this way are present in the form of diastereoisomers, with their tetralin ring containing asymmetric carbon atoms at the 2- and 4-positions.

When the mixture of the diastereoisomers is fused under heating at 60° to 200° C., preferably 100° to 140° C., the 2,4-cis isomer (simply referred to as "cis-isomer") causes ring closure to form 1,4-methano-2-benzazepin-3-one derivative of the formula:

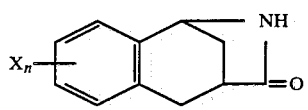

(V)

wherein X and n are the same as above. Since the compound of formula (V) is neutral, the 2,4-trans isomer (simply referred to as "trans-isomer") can be isolated by the extraction with acid or alkali. The compounds of formula (V) can be converted, upon hydrolysis by acid or alkali, into the cis-isomer of amino-acid.

The cis-isomer and the trans-isomer thus separated are respective racemates, and the racemates can be separated into respective optically active isomers, for example by optically resolving the ester compounds with an optically active carboxylic acid, e.g. tartaric acid, dibenzoyltartaric acid, camphorsulfonic acid, diacetyltartaric acid, phenylsuccinic acid, mandelic acid, malic acid, lactic acid, etc. or the amino-protected carboxylic acid compound with an optically active base (e.g. natural alkaloid such as brucine, quinine, cinchonidine, etc., optically active α-phenethylamine, α-amino acid ester, etc.).

Where a carboxylic acid compound of formula (II), (III) or (IV) optically active at the 2-position is used, respective optical isomers can be obtained only through the foregoing procedure of separation into the cis-isomer and the trans-isomer.

The compounds (I) of the invention may be, if desired, treated with acid (e.g. inorganic acid such as hydrochloric acid, sulfuric acid, phosphoric acid, nitric acid, or organic acid such as acetic acid, oxalic acid, maleic acid, fumaric acid, lactic acid, citric acid, etc.) or with inorganic base (e.g. sodium hydroxide, sodium bicarbonate, potassium hydroxide, calcium hydroxide, etc.) to form their acid or base adducts.

As will be apparent from the description above, the compounds (I) of this invention include all of the diastereoisomers, cis-isomers, transisomers and optically active isomers and salts thereof.

The diuretic activity of the compounds (I) according to this invention will be shown hereinbelow. The transisomers have more potent activity than the cis-isomers.

Test Method

According to the method of Lipschitz et al (W. L. Lipschitz, Z. Haddian, A. Kerpsser: J. Pharmacol. 79, 97 (1943)), groups each of 6 male Wistar rats (weighing 180 to 220 g) were used. In preconditioning, they were not fed with any food for 18 hours and further with any food and water for 3 hours. Test group of the rats was orally administered with a solution or suspension of the test compounds of this invention in isotonic saline at a dosage of 25 ml/kg and was placed in metabolism cages, and urine of them was collected in the course of 6 hours.

The diuretic activity is calculated by the following equation in terms of increment percentage of the test group to control group:

$$\frac{\left(\begin{array}{c}\text{Average urine amount}\\\text{of test group}\end{array}\right) - \left(\begin{array}{c}\text{Average urine amount}\\\text{of control group}\end{array}\right)}{(\text{Average urine amount of control group})} \times 100 = \text{increment percentage}$$

| Results | |
|---|---|
| Compound (Example No.) | Increment (%) |
| 1(a) | 737 |
| 2 | 410 |
| 3 | 900 |
| 4 | 90 |
| 7 | 362 |
| 14 | 225 |
| 16 | 441 |
| 17 | 436 |
| 18 | 354 |
| 19 | 241 |

Under the same test conditions above, 4-amino-1,2,3,4-tetrahydro-2-naphthoic acid hydrochloride, methyl trans-4-amino-1,2,3,4-tetrahydro-2-naphthoate hydrochloride, ethyl trans-4-amino-6,7-dimethoxy-1,2,3,4-tetrahydro-2-naphthoate hydrochloride did not show any results significantly different from the control group. With GABA per se, the diuretic activity could not be found even at a high dosage of 1000 mg/kg.

Blood pressure lowering action due to the compound of Example 1a which is typical of this invention is shown in the following:

Test Method (1) Experiment with Spontaneous Hypertensive Rats (SHR)

Spontaneous hypertensive male rats (SHR) of 28 to 30 weeks age were used for the experiment and blood pressure was measured according to tail compressing method. These rats were preliminarily divided into control group and test group (six rats/one group) so that both the groups have the same mean blood pressure.

A suspension of the test compound in 0.5% methylcellulose solution was administered orally to the test group at a dosage of 2 ml/kg and after 1, 5, 7 and 9 hours blood pressure was measured. Dosage required for lowering the blood pressure value before the administration by 20 mm Hg was determined.

(2) Experiment with DOCA Hypertensive Rats

According to the method of Willard, male Wistar rats of 8 weeks age were made DOCA (deoxycorticosterone acetate) hypertensive rats by operation and among them, rats whose blood pressure values after 6 weeks had reached upward of 150 mm Hg were used as test animal.

The experiment was carried out in the same conditions as those of SHR above.

| Results | | |
|---|---|---|
| | SHR | DOCA |
| $ED_{20}$ (mg/kg, p.o.) | 10 | 6.5 |

In both the Experiments, the blood pressure lowering action was generally and slowly exhibited and its maximum effect was exerted 7 to 9 hours after the administration of the test compound.

The compounds of formula (I) of this invention can be administered orally or parenterally as pharmaceutical composition by the combination with a suitable, conventional pharmaceutically acceptable carrier. The pharmaceutical composition may be the form of tablets, capsules, granules, powders, injectable solutions or the like.

The daily dose of the compounds (I) for human adults ranges usually from about 10 mg to about 500 mg for oral administration in single dose or multiple doses, but may vary depending on the age, weight and/or conditions of disease to be treated and response to the medication.

The invention will be hereinafter described more concretely by the following examples, but they are not to be construed as limiting the invention.

EXAMPLE 1

(a) A solution of 265 g of ethyl 7,8-dichloro-4-hydroxyimino-1,2,3,4-tetrahydro-2-naphthoate (m.p. 133°–135° C.) in 1 l of ethanol is charged into 3l-autoclave and 130 ml of 12% ethanolic ammonia and 27 g of Raney nickel are added thereto to reduce with hydrogen under pressure of 65 atm at an inner temperature of 75° C. The hydrogen uptake is completed in about 3 hours, and then the whole is allowed to cool. The catalyst is filtered off and the filtrate is concentrated. Ethyl acetate is added to the residue and cooled. Crystals are deposited and collected by filtration to give 75 g of 6,7-dichloro-1,4-methano-2,3,4,5-tetrahydro-1H-2-benzazepin-3-one, m.p. 196°–200° C., which is ring-closure product of the foregoing cis-isomer. The filtrate solution is washed with water once, dried and concentration under heating on oil-bath at 130° C. for 3 hours. After cooling, ethyl acetate is added and the deposited crystals are collected by filtration to recover an additional 14 g of the ring-closure isomer. The filtrate solution is diluted with 1 l of ethyl acetate and 150 ml of 20% aqueous hydrochloric acid is added with stirring, whereupon white needles separate out. The crystals are collected by suction filtration to give 76 g of crude ethyl trans-4-amino-7,8-dichloro-1,2,3,4-tetrahydro-2-naphthoate hydrochloride. The aqueous layer of the filtrate solution is separated, the organic layer is extracted with water several times and the aqueous layers combined are saturated with sodium chloride. An additional 23 g of crystalline product is recovered. The product, when recrystallized from ethanol, shows a m. p. of 249°–251° C. (decomposition).

(b) Ethyl trans-4-amino-7,8-dichloro-1,2,3,4-tetrahydro-2-naphthoate, when optically resolved by dibenzoyl-D-tartaric acid and dibenzoyl-L-tartaric acid, affords optically active dextro- and lovo-isomers, respectively.

Hydrochloride of dextro-isomer: m.p. 209°–213° C. $[\alpha]_D = +38.6$ (1%, methanol).

Hydrochloride of levo-isomer: m.p. 208°–213° C. $[\alpha]_D = -37.4$ (1%, methanol).

EXAMPLE 2

A suspension of 29 g of 6,7-dichloro-1,4-methano-2,3,4,5-tetrahydro-1H-2-benzazepin-3-one in 300 ml of 20% hydrochloric acid is hydrolyzed by heating with stirring for 40 hours. After cooling, crystals are precipitated and collected by filtration to give 32 g of crude cis-4-amino-7,8-dichloro-1,2,3,4-tetrahydro-2-naphthoic acid hydrochloride. To the crude product is added 500 ml of ethanol, and dry hydrochloric acid gas is introduced gently with stirring under reflux for 8 hours. After cooling, crystals are deposited, separated by filtration and recrystallized from 95% ethanol to give 29 g of ethyl cis-4-amino-7,8-dichloro-1,2,3,4-tetrahydro-2-naphthoate hydrochloride having a m.p. of 239°–245° C. (decomposition) as white needles.

EXAMPLE 3

A solution of 60 g of methyl 6,7-dichloro-4-hydroxyimino-1,2,3,4-tetrahydro-2-naphthoate in 300 ml of methanol and 300 ml of 10% ammonia-methanol is hydrogenated at 60 atm of hydrogen in the presence of Reney nickel. Heating is conducted at 70°–80° C. with stirring for 7 hours. After cooling, the catalyst is filtered off and the solvent is distilled off. Acetone is added to the semi-solid residue and cooled. The precipitated crystals are collected by filtration to give 17 g of 7,8-dichloro-1,4-methano-2,3,4,5-tetrahydro-1H-2-benzazepin-3-one, m.p. 215°–217° C. The mother liquor is concentrated, heated at 110°–120° C. for 2 hours and cooled followed by crystallization from acetone. Upon filtration, additional 3 g of ring-closure product is obtained. The mother liquor is concentrated, and ethyl acetate and 100 ml of 10% aqueous hydrochloric acid are added and stirred well. White needles are deposited and collected by filtration to give 10 g of methyl trans-4-amino-6,7-dichloro-1,2,3,4-tetrahydro-2-naphthoate hydrochloride in the crystalline form. From the mother liquor, a further 3 g of the product is recovered. The product, upon recrystallization from methanol, gives white needles having a m.p. of 262°–263° C. (decomposition).

EXAMPLE 4

Into a solution of 3.6 g of methyl trans-4-amino-6,7-dichloro-1,2,3,4-tetrahydro-2-naphthoate hydrochloride in 50 ml of methanol and 15 ml of 28% aqueous ammonia, ammonia gas is blown at 30°–40° C. for 8 hours. The solvent is distilled off and water is added. The precipitated crystals are separated by filtration and dissolved in methanol and to the solution is added methanolic hydrochloric acid. Crystals are deposited, separated by suction filtration and recrystallized from methanol to give 1.6 g of trans-4-amino-6,7-dichloro-1,2,3,4-tetrahydro-2-naphthalene carboxamide hydrochloride having a m.p. of above 280° C.

EXAMPLE 5

To a solution of 1.5 g of methyl trans-4-amino-6,7-dichloro-1,2,3,4-tetrahydro-2-naphthoate in 20 ml of pyridine is added 10 ml of acetic anhydride under ice-cooling, and the reactant is allowed to stand overnight. The reaction solution is concentrated and to the resulting residue is added water. Deposited crystals are separated by suction filtration and recrystallized from ethanol to give 1.5 g of methyl trans-4-acetamide-6,7- dichloro-1,2,3,4-tetrahydro-2-naphthoate, m.p. 182°–184° C.

EXAMPLE 6

Into 100 ml of 50% methanol, 3.1 g of methyl trans-4-6,7-dichloro-1,2,3,4-tetrahydro-2-naphthoate hydrochloride is dissolved under warming, and to the solution is added dropwise a solution of 1.2 g of potassium cyanate in 10 ml of water. After the dropwise addition, the system is made to react at 60° C. for 2 hours and cooled with ice. Deposited crystals are separated by filtration, washed with water, and recrystallized from a mixture of methanol and acetone to give 1.7 g of methyl trans-6,7-dichloro-4-ureido-1,2,3,4-tetrahydro-2-naphthoate having a m.p. of 227°–229° C.

The following compounds are produced in a similar manner to Examples 1 to 6.

7. Methyl trans-4-amino-6-chloro-1,2,3,4-tetrahydro-2-naphthoate hydrochloride, m.p. 229°–231° C.
8. Methyl cis-4-amino-6-chloro-1,2,3,4-tetrahydro-2-naphthoate hydrochloride ½ hydrate, m.p. 218°–219° C. (decomposition)
9. Cis-4-amino-6-chloro-1,2,3,4-tetrahydro-2-naphthoic acid hydrochloride, m.p. 269°–271° C. (decomposition)
10. Ethyl trans-4-amino-6-chloro-1,2,3,4-tetrahydro-2-naphthoate hydrochloride, m.p. 199°–200° C.
11. Trans-4-amino-6-chloro-1,2,3,4-tetrahydro-2-naphthoic acid hydrochloride, m.p. 283°–285° C.
12. Methyl trans-4-amino-7-chloro-1,2,3,4-tetrahydro-2-naphthoate hydrochloride, m.p. 215°–218° C.
13. Cis-4-amino-6,7-dichloro-1,2,3,4-tetrahydro-2-naphthoic acid hydrochloride, m.p. 256°–257° C.
14. Trans-4-amino-6,7-dichloro-1,2,3,4-tetrahydro-2-naphthoic acid hydrochloride, m.p. 283°–285° C.
15. Ethyl cis-4-amino-6,7-dichloro-1,2,3,4-tetrahydro-2-naphthoate hydrochloride, m.p. 222°–223° C.
16. Ethyl trans-4-amino-6,7-dichloro-1,2,3,4-tetrahydro-2-naphthoate hydrochloride, m.p. 234°–236° C.
17. Methyl trans-4-amino-7,8-dichloro-1,2,3,4-tetrahydro-2-naphthoate hydrochloride, m.p. 247°–250° C. (decomposition)
18. Methyl cis-4-amino-7,8-dichloro-1,2,3,4-tetrahydro-2-naphthoate hydrochloride, m.p. 240°–242° C. (decomposition)
19. Butyl trans-4-amino-7,8-dichloro-1,2,3,4-tetrahydro-2-naphthoate hydrochloride, m.p. 163°–167° C.
20. Ethyl trans-4-amino-6-fluoro-1,2,3,4-tetrahydro-2-naphthoate hydrochloride, m.p. 211°–213° C.
21. Ethyl trans-4-amino-6-bromo-1,2,3,4-tetrahydro-2-naphthoate The invention has been fully explained in the description and examples given above, but any variations and modifications of it may be made without departing from the spirit and scope of the invention.

We claim:

1. 4-Amino-1,2,3,4-tetrahydro-2-naphthoic acid derivatives of the formula:

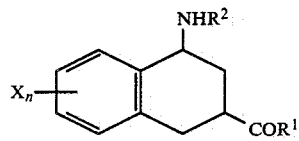

or salts thereof, wherein X is halogen atom, n is 1 or 2, $R^1$ is hydroxy group, $C_1$ to $C_4$ alkoxy group or amino group, and $R^2$ is hydrogen atom.

2. The compound as claimed in claim 1, which is ethyl trans-4-amino-7,8-dichloro-1,2,3,4-tetrahydro-2-naphthoate.
3. The compound as claimed in claim 1, which is ethyl cis-4-amino-7,8-dichloro-1,2,3,4-tetrahydro-2-naphthoate.
4. The compound as claimed in claim 1, which is methyl trans-4-amino-6,7-dichloro-1,2,3,4-tetrahydro-2-naphthoate.
5. The compound as claimed in claim 1, which is methyl trans-4-amino-6-chloro-1,2,3,4-tetrahydro-2-naphthoate.
6. The compound as claimed in claim 1, which is ethyl trans-4-amino-6,7-dichloro-1,2,3,4-tetrahydro-2-naphthoate.
7. The compound as claimed in claim 1, which is methyl trans-4-amino-7,8-dichloro-1,2,3,4-tetrahydro-2-naphthoate.
8. The compound as claimed in claim 1, which is methyl cis-4-amino-7,8-dichloro-1,2,3,4-tetrahydro-2-naphthoate.
9. A pharmaceutical composition comprising a therapeutically effective amount of said compound as claimed in claim 1 and a pharmaceutically acceptable carrier.

* * * * *